United States Patent
Weiss

(10) Patent No.: US 7,730,572 B2
(45) Date of Patent: Jun. 8, 2010

(54) CONTINUOUS FEED INTER-DENTAL BRUSH AND DEVICE

(76) Inventor: Roger E. Weiss, 1742 Naudain St., Philadelphia, PA (US) 19146

( * ) Notice: Subject to any disclaimer, the term of this patent is extended or adjusted under 35 U.S.C. 154(b) by 870 days.

(21) Appl. No.: 11/602,006

(22) Filed: Nov. 20, 2006

(65) Prior Publication Data
US 2008/0115799 A1 May 22, 2008

(51) Int. Cl.
*A61C 15/00* (2006.01)
(52) U.S. Cl. .................. 15/167.1; 15/169; 15/172; 15/184; 132/328; 132/321
(58) Field of Classification Search .............. 15/167.1, 15/169, 172, 184, 194, 201, 202, 206; 132/321, 132/328; *A61C 15/00*
See application file for complete search history.

(56) References Cited

U.S. PATENT DOCUMENTS

| | | | | |
|---|---|---|---|---|
| 3,886,956 A | | 6/1975 | Cash | 132/91 |
| 4,005,721 A | | 2/1977 | Yasumoto | 132/91 |
| 4,245,658 A | | 1/1981 | Lecouturier | 132/322 |
| 4,512,354 A | | 4/1985 | Loubier et al. | 132/91 |
| 5,060,681 A | | 10/1991 | Westbrook | 132/325 |
| 5,085,236 A | | 2/1992 | Odneal et al. | 132/325 |
| 5,176,157 A | | 1/1993 | Mazza | 132/322 |
| 5,217,031 A | | 6/1993 | Santoro | 132/322 |
| 5,269,331 A | | 12/1993 | Tanriverdi | 132/325 |
| 5,316,028 A | * | 5/1994 | Flemming | 132/329 |
| 5,495,863 A | | 3/1996 | Bergman | 132/326 |
| 5,505,216 A | * | 4/1996 | Gilligan et al. | 132/321 |
| 5,613,508 A | * | 3/1997 | Bushman | 132/325 |
| 5,642,741 A | | 7/1997 | Choi | 132/329 |
| 5,657,780 A | * | 8/1997 | Giacopuzzi | 132/325 |
| 5,718,667 A | | 2/1998 | Sugimoto et al. | 601/139 |
| 5,722,440 A | | 3/1998 | Urso | 132/323 |
| 5,857,471 A | * | 1/1999 | Harada | 132/321 |
| 5,868,149 A | | 2/1999 | Yang | 132/328 |
| 6,079,424 A | | 6/2000 | Lillbacka | 132/326 |
| 6,363,949 B1 | | 4/2002 | Brown | 132/325 |
| 7,011,099 B2 | * | 3/2006 | Bergman | 132/325 |

(Continued)

FOREIGN PATENT DOCUMENTS

JP 08-056749 3/1996

(Continued)

*Primary Examiner*—Monica S Carter
*Assistant Examiner*—Stephanie Newton
(74) *Attorney, Agent, or Firm*—Ernest D. Buff & Associates, LLC.; Ernest D. Buff; Harry Anagnostopoulos

(57) ABSTRACT

An inter-dental brush is provided with a handle that accepts a cartridge housing continuous inter-dental brush feedstock. Used, worn out brush is cut off by a slidable cutter provided on an angled portion of the handle. Fresh inter-dental brush is fed out from the continuous inter-dental feedstock by turning a knob on the handle. The protrusion length of the inter-dental brush is controlled by the number of turns. The knob is connected to a gear that pushes against the feedstock, driving the brush through an aperture in the angled portion of the handle. Within the cartridge, the feedstock is removably attached to one swivel and is wrapped around a second swivel. The swivels have a brake that produces a taut feedstock as the brush is fed out. The cartridge may contain a single roll with a brake instead of a pair of swivels.

15 Claims, 3 Drawing Sheets

U.S. PATENT DOCUMENTS

| | | | |
|---|---|---|---|
| 2005/0000539 A1 | 1/2005 | Bergman | 132/325 |
| 2005/0144747 A1 | 7/2005 | Jaun | 15/167.1 |
| 2005/0247328 A1 | 11/2005 | Shen et al. | 132/325 |
| 2006/0011211 A1 | 1/2006 | Landry | 132/325 |
| 2006/0011212 A1 | 1/2006 | Achepohl et al. | 132/325 |

FOREIGN PATENT DOCUMENTS

| | | |
|---|---|---|
| JP | 2004-313446 | 11/2004 |

* cited by examiner

CONTINUOUS FEED INTER-DENTAL BRUSH AND DEVICE

BACKGROUND OF THE INVENTION

1. Field of the Invention

The present invention relates to a brush for improving dental hygiene; and, more particularly, to a device wherein a continuous feed of inter-dental brush is swiveled around a pair of swivels housed within a handle to provide a mechanism for continuous feed of inter-dental brush that enables excision of used inter-dental brush and the production of fresh inter-dental brush upon demand.

2. Description of the Prior Art

Devices for cleaning teeth and removing plaque that is accumulated between teeth are well known in the art. Most commonly used devices include electrically powered toothbrushes, dental floss and inter-dental tooth cleaning brushes. These inter-dental toothbrushes are more effective when the gaps between teeth are adequate for the insertion of the inter-dental brush, and the gaps between teeth are readily accessible. In these cases, where the gaps between the teeth are large, use of dental floss in removing plaque is generally ineffective since the floss fails to contact the entire root surface of the teeth. Inter-dental brushes have become popular in recent times, since they effectively remove plaque that has accumulated between teeth and around the entire tooth-gum interface, which is not readily removed using dental floss.

Numerous patents disclose dental floss holders having means to feed new floss, collect used floss and adjust tension in the dental floss. Very few patents relate to inter-dental brushes. These patents require discrete brushes attached to metallic wire designed for insertion into a slot carried by the brush handle. In this manner, replacement is effected for discrete inter-dental brushes that have become worn. None of the patents envision the use of a cutter to cut off a used, worn out inter-dental brush and/or the replacement of a used inter-dental brush with a fresh inter-dental brush from a continuous feed stock.

U.S. Pat. No. 3,886,956 to Cash discloses a dental floss holder. This floss holder has a cavity that holds a spool of dental floss and delivers it to the floss head through a pair of pincers that grip the dental floss. The pincers are opened by application of finger pressure to a button provided on the handle of the floss holder. The '956 patent does not disclose delivery of fresh inter-dental brush; it does not disclose means for cutting used inter-dental brush prior to exposing fresh inter-dental brush.

U.S. Pat. No. 4,005,721 to Yasumoto discloses a dental floss holder. The interior of the dental floss holder has a cavity for retaining the dental floss spool. The dental floss is connected to a bifurcated tip, which may be sideways mounted for accessing front teeth, and a bottom-mounting tip for cleaning back teeth. The '721 patent contains no disclosure regarding delivery of inter-dental brush. No means are provided for cutting used inter-dental brush prior to exposing fresh dental brush.

U.S. Pat. No. 4,512,354 to Loubier et al. discloses a dental floss applicator with improved floss severing and anchoring. This dental floss applicator has a capstan controllable by the user for tensioning the floss and for periodically substituting a fresh floss strand segment for a previously used segment. An improved arrangement is provided, whereby floss is severed, and a floss strand end is anchored to the capstan by continuous movement of the strand. Such disclosure of a dental floss applicator handle having means for cutting the floss does not suggest delivery of inter-dental brush from a continuous feed.

U.S. Pat. No. 5,060,681 to Westbrook et al. discloses a dental flossing device. This device uses a continuous dental floss that is fed from a spool to a dental floss head. Used floss is returned to an adjacent spool and both spools are located in the handle. When the supply of fresh floss on the bobbin is exhausted, the device is discarded. The dental flossing device does not deliver inter-dental brush.

U.S. Pat. No. 5,085,236 to Odneal et al. discloses a dental floss machine. This dental floss machine attaches to a standard electric toothbrush to provide oscillatory motion of the floss. The floss spool is contained within the handle of the machine and the used floss is collected in a separate spool that is on the same shaft as the dental floss supply spool. This dental floss machine does not deliver inter-dental brush. It does not have means for cutting used inter-dental brush prior to exposure of fresh dental brush.

U.S. Pat. No. 5,176,157 to Mazza discloses a device for supporting and operation a dental floss. The dental floss is contained within the handle. A motor drive is provided to drive the dental floss into a flossing fork and the used floss is collected within the handle. The motor, in addition to providing drive for the dental floss, also provides a vibratory motion imparted by an RF coil. This dental floss device does not deliver inter-dental brush. It does not have means for cutting used inter-dental brush prior to exposing fresh dental brush.

U.S. Pat. No. 5,217,031 to Santoro discloses a motor-driven apparatus for cleaning spaces between teeth by dental floss. This motor-driven apparatus is operative to clean spaces between teeth with dental floss. A motor drive feeds fresh dental floss, collects used dental floss in the pulley and also provides oscillation to the taut dental floss. This device does not deliver inter-dental brush. No means are provided for cutting used inter-dental brush and exposing a fresh inter-dental brush segment.

U.S. Pat. No. 5,269,331 to Tanriverdi discloses an automatic locking and adjustable tension controlled dental flosser. This self-contained dental flosser has an adjustable tension control. An auto-tension locking mechanism allows the flosser to operate and advance the floss continuously in one direction by rotating a spool wherein spool gears extend out of the main frame. This flosser uses dental floss and delivers fresh floss, while at the same time removing used floss into two separate spools contained within the handle of the flosser. This flosser does not provide for delivery of inter-dental brush. It does not have means for cutting used inter-dental brush and exposing a fresh inter-dental brush segment.

U.S. Pat. Nos. 5,495,863 and 7,011,099 to Bergman disclose a flossing device with advancing and tensioning mechanisms. U.S. Published Patent Application No. 2005/0000539 to Bergman discloses a hand held flossing device. The floss is delivered using a one-way ratchet gear from a dental floss spool contained within the handle. After delivery, the used floss is returned back to a shaft that carries the advancing gear, where the used floss is stored. A separate mechanism adjusts the tension of the taut dental floss. This flossing device does not provide for delivery of inter-dental brush. It contains no means for cutting used inter-dental brush and exposing fresh inter-dental brush.

U.S. Pat. No. 5,642,741 to Choi discloses a toothpick. A spiral wound wire toothpick is coated with a resin. It is attached to a main body for easy grasping of the toothpick. The '741 patent does not disclose delivery of inter-dental brush. No disclosure is contained therein concerning means for cutting and exposing a fresh inter-dental brush.

U.S. Pat. No. 5,657,780 to Giacopuzzi discloses a dental floss holder having a wedge actuated brake assembly. The handle of the dental floss holder has a supply real that delivers the dental floss to the holding sections, while used dental floss is returned to a take up reel. A brake assembly adjusts the tension of the dental floss. No disclosure is contained by the '780 patent concerning delivery inter-dental brush and/or means for cutting and exposing a fresh inter-dental brush.

U.S. Pat. No. 5,718,667 to Sugimoto et al. discloses an oral hygiene instrument. An oral hygiene tool is removably attached to a holder member with a vibration generating means that vibrates the instrument by way of the holder member. This oral hygiene instrument uses an inter-dental cleaning brush or instruments such as tooth brush, a nipple-type gum massaging tool, a gum massaging tool or a floss unit attached to one end of the instrument through a plurality of slits. The instrument has a central cavity that houses a battery and a vibrating generating means. The cavity is closed by a screwed-on end cap with a watertight seal. An inter-dental cleaning brush or other oral hygiene instruments are vibrated. They have to be attached one at a time using the plurality of slots provided. No disclosure is contained within the '667 patent concerning a dedicated instrument for an inter-dental cleaning brush. The hygiene instrument does not provide new brush elements that may be advanced from a continuous feed stock, with the worn out portion of the inter-dental cleaning brush being clipped and discarded.

U.S. Pat. No. 5,722,440 to Urso discloses a bite device for driving floss through tight inter-dental gaps. A flossing aid drives a spanned dental floss between the fork of a flossing device. A leaf spring loaded bitable button drives the floss between teeth with small inter-dental space. When the bite is released, the leaf spring pushes the biting element away, permitting flossing operation. No disclosure is contained with the '440 patent concerning an inter-dental brush.

U.S. Pat. No. 5,868,149 to Yang discloses a retractable toothpick. An expanding bi-toothpick has dual controls for pushing and extracting. The retractable toothpick is a slender flexible rod inserted into a curved tube attached to a spring-like V shaped element. Moving the V shaped element pushes the inner toothpick rod in and out between the interstices of the teeth, removing occluded food particles. This retractable toothpick is structurally and functionally distinct from an inter-dental brush that may be refreshed from a continuous brush feed stock.

U.S. Pat. No. 6,079,424 to Lillbacka discloses a method and arrangement for tensioning dental floss, and a device for cleaning teeth. This device and method is operative to hold and tension dental floss. A tensioning element rotates within the device body; a tensioning passage and a guide passage are located at opposite ends of the tensioning element. The tensioning passage and the guide passage are offset by an angle, which allows the floss to be secured when the tensioning element is rotated, without introducing excessive tension in the strand. This device uses a dental floss which may be withdrawn from a spool and tightened. There is no disclosure in the '424 patent concerning an inter-dental brush that may be renewed from a continuous inter-dental brush feedstock.

U.S. Pat. No. 6,363,949 to Brown discloses a dental care device. This dental care device combines a flossing tool for dispensing dental floss and holding a length of the floss under tension with a double-edged tongue scraper. The dental care device includes an ergonomic handle. The handle includes a tool storage compartment, which may be used to contain dental hygiene tools such as a microbrush and a pick. The tongue scraper is attached to the end of the handle opposite the floss fork and includes a semicircular blade having opposing edges which are formed so that one of the edges is sharper than the other. This dental care device includes a flossing element on one side and a tongue scraper on the other side. Such a device does not operate to suggest an inter-dental brush. The microbrush provided in the tool storage section of the device does not provide the functionality of an inter-dental brush. No disclosure is contained by the '949 patent concerning a replaceable inter-dental brush that is fed out from a continuous inter-dental brush feed stock.

U.S. Published Patent Application No. 2005/0144747 to Juan discloses an inter-dental brush structure. This inter-dental brush structure comprises a brush shaft installation opening installed on the curved end of the brush handle. A fitting bulge and a joined clip lid are installed on the top surface of the curved end. The joined clip lid has a fitting fillster installed, matching the fitting bulge. The fitting fillister of the joined clip lid can fit the fitting bulge and fix the brush shaft inserted in the brush shaft installation opening by pushing back the rear of the brush shaft and clipping it tight to fix, and in turn enable, the installation and replacement of the brush shaft. The brush handle in formed of two parts connected by an axis so that it can revolve. The connecting surface has several indents and bulges arranged in a circle to fix the location of the revolving handle. The characteristic of this inter-dental brush structure comprises an adjustment to the angle, which is needed for brushing the rear teeth crevices, thereby increasing the convenience of usage. This inter-dental brush accepts new brush elements, which are held in place by a joining clip connected to the rim of the curved surface of the handle. The handle can be rotated to various orientations for inter-dental brushing of hard to reach teeth. The inter-dental brushes are separate elements that are crimped by the joining clip. This structure does not replace inter-dental brushes from a continuous inter-dental brush feed stock.

U.S. Published Patent Application No. 2005/0247328 to Shen et al. discloses a dental floss holder. This dental floss holder has a spool of dental floss contained within the handle body, so that the dental floss head can be moved up and down. This dental floss holder does not dispense inter-dental brush.

U.S. Published Patent Application No. 2006/0011211 to Landry discloses a dental floss dispensing and tensioning device. A hand-held dental floss holder, dispenser, floss tensioning, and floss advancing device are disclosed. The handle of the device carries a dental floss spool. Dental floss passes through the fork of the dental flosser and is collected in a collection spool. The floss tension is adjusted by a clutch gear. This '211 device does not does not disclose or suggest use of an inter-dental brush.

U.S. Published Patent Application No. 2006/0011212 to Achepohl et al. discloses a manual advance dental floss holder. This holder has a spool of dental floss, which is fed to the flossing head. Used floss is collected in a spool within the handle. The dental floss is manually advanced and its tension is manually adjusted. The '212 patent does not use an inter-dental brush.

Foreign Patent Application No. JP 08-056749 to Kageyama et al. discloses a sanitary article holding device. A holding device is provided wherein a sanitary article can be replaced cleanly, and which provides favorable usage operation. The sanitary article is a toothbrush; not an inter-dental brush. The brush is ejected from a holder, as opposed to being cut. Each brush is an individual piece; the brush is not made available from a continuous feedstock of inter-dental brush.

Foreign Patent Application No. JP 2004-313446 to Ikemoto discloses an inter-dental cleaning implement. A brush is attached to a metallic rod and slides through a storage device. The storage device has a slot through which a projecting end of the metallic rod can slide to move the inter-dental brush through an opening in the teeth. The brush is not said to be removable from the metallic rod. It is not delivered from a continuous feedstock of inter-dental brush.

Notwithstanding the efforts of prior art workers to construct a dental hygiene device, and particularly an inter-dental cleaning brush device, there exists a need in the art for facile removal of a worn inter-dental brush and rapid replacement thereof with a fresh inter-dental brush without having to stick metallic wires and rods carrying discrete brush segments into slots within the device handle. Ready replacement of worn inter-dental brushes would encourage use of the device, thereby promoting improved oral hygiene even in cases where inter-tooth gaps exist.

SUMMARY OF THE INVENTION

The present invention provides an inter-dental brush that is especially suited for use in cases where inter-tooth gaps exist. The inter-dental brush is easy to use and readily refreshed when worn by new inter-dental brush advanced from continuous feed stock. Removal of a worn inter-dental brush and replacement thereof with a fresh inter-dental brush is effected in an efficient, economical manner. Manually challenging maneuvers previously required when sticking metallic wires and rods carrying discrete brush segments into slots within the device handle are virtually eliminated. Ready replacement of worn inter-dental brushes encourages use of the inter-dental brush device, and improved oral hygiene is promoted.

Generally stated, the inter-dental device comprises a handle with an angular portion. An inter-dental brush protrudes from the angled portion of the handle, ready for use. A cutter is provided at the angular portion of the handle proximal to the inter-dental brush attachment point. When the user perceives that the inter-dental brush is worn, the cutter is used to snip off the worn segment of the inter-dental brush. The user then turns a knob provided on the handle which, in turn, activates a gear mechanism that drives a continuous feed of inter-dental brush. A continuous filament of inter-dental feedstock is held taut between two swivels. The fresh inter-dental brush is contained taut between two swivels within a replaceable cartridge that is contained within the handle of the device. Advancing the inter-dental feedstock causes fresh inter-dental brush to protrude from the handle. The protrusion length of the inter-dental brush is controlled by the extent to which the knob in the handle is turned by the user.

The continuous feed of inter-dental brush has a central wire which carries the inter-dental brush. If the brush is squeezed very hard, the brush elements may collapse. In order to provide the required drive for the continuous feed of the inter-dental brush, the load applied must be small. Therefore, a gear mechanism is used, and the teeth of the gear penetrate into the inter-dental brush feedstock, pushing out the inter-dental brush. The brush recovers its original shape due to the resiliency of the brush elements attached to the central wire element of the inter-dental brush.

The replaceable cartridge contains a long length of the inter-dental brush feedstock that is removably attached to one of the rotatable swivels and wrapped around a second rotatable swivel. Inter-dental feedstock is wrapped several times, thereby surrounding the first swivel and the second swivel several times. Due to large angle of wrap of each of the layers the feedstock around the swivels, sufficient friction is generated that the feedstock is held taut as the gear feeds out the continuous inter-dental brush feedstock. The swivels may be retarded by a friction generating brake to prevent free running thereof as the feedstock is fed out. The typical angle of wrap around the swivels is in the range of 150 to 200 degrees, preferably approximately 180 degrees. The free end of the feedstock is inserted into the gear mechanism, which is lined with an aperture in the angled portion of the handle so that the inter-dental brush feedstock is fed out when the knob attached to the gear is activated by the user. While the preferred embodiment of the invention uses two swivels around which continuous feedstock of the inter-dental brush is wrapped, a second embodiment of the invention uses a single roll for feeding the feedstock to the gear mechanism. The single roll may be retarded by a brake, which generates friction and prevents free running of the single roll.

Prior to feeding out fresh inter-dental brush from the continuous feedstock, substantially all of the used, worn out inter-dental brush must be snipped off. This is accomplished by using a slidable cutter provided on the angled portion of the handle. The slidable cutter has a sharp edge provided at its underside surface, which cuts off the metallic wire of the inter-dental brush. The slidable cutter is pushed back into the angled portion of the handle after this cutting operation.

BRIEF DESCRIPTION OF THE DRAWING

The invention will be more fully understood and further advantages will become apparent when reference is had to the following detailed description of the preferred embodiments of the invention and the accompanying drawings, in which.

DETAILED DESCRIPTION OF THE INVENTION

Figure 1:
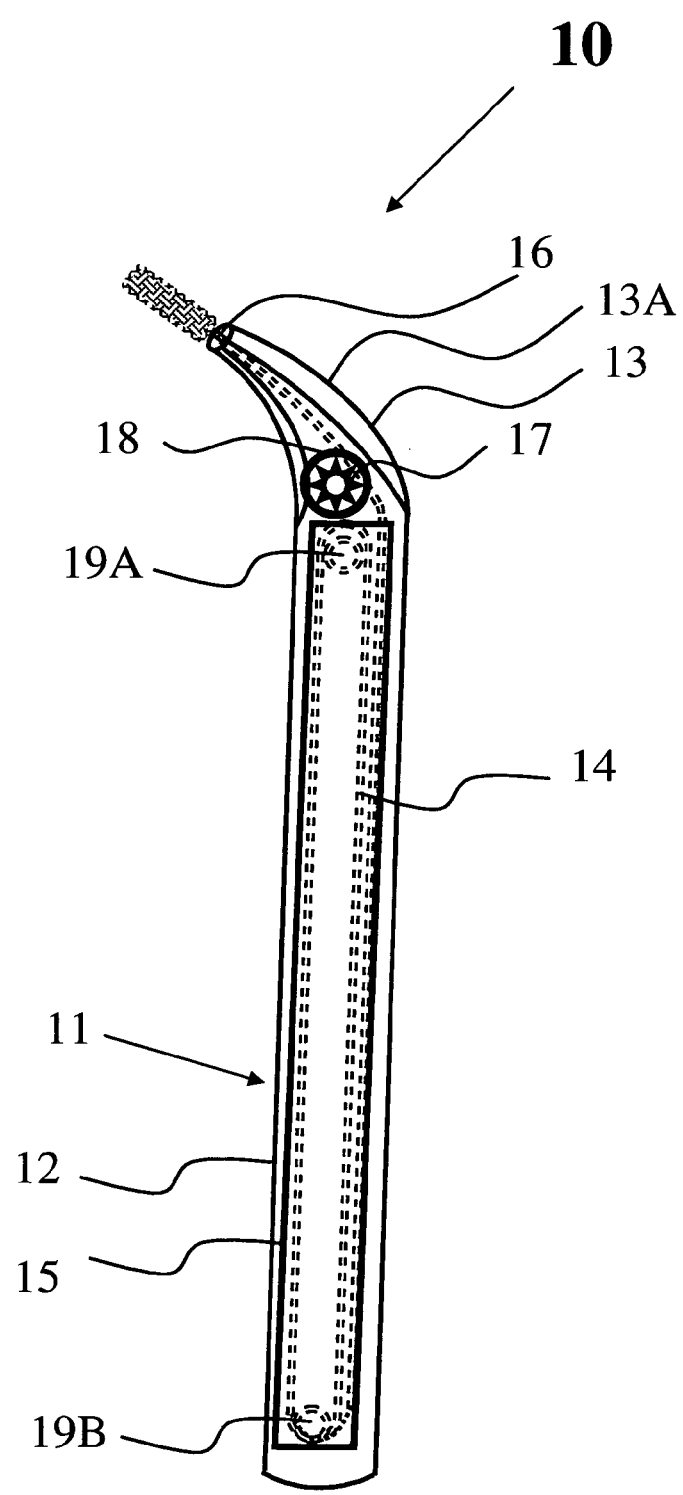
FIG. 1 depicts a side view of the inter-dental brush device showing continuous feedstock of inter-dental brush material delivered by a gear drive and feedstock contained within a replaceable cartridge having a pair of swivels.

This invention relates to a continuous feed inter-dental brush and device that provides fresh segments of inter-dental brush from a cartridge contained within the handle of the device. A continuous feed is effectuated, and the fresh segments are delivered, by turning a knob that drives a continuously wound supply of brush contained within a cartridge located within the handle of the device. The worn out brush portion is cut by the user using a slidable knife before turning the brush delivery knob.

Generally stated, the invention comprises a continuous feed inter-dental brush and device. The inter-dental device is particularly suited for use by those persons concerned with the treatment and/or prevention of gum disease. The inter-dental device is equipped with an internal brush cartridge that effectuates a continuous feed of brush to the user. In this manner, there is provided a more sanitary, more effective, longer lasting, and more economical apparatus. Use of the inter-dental device facilitates maintenance of proper oral hygiene. It promotes the health and beauty of the mouth, gums, and teeth.

There are many products and devices on the market, which help people maintain hygiene within the oral cavity. Such products include toothbrushes, floss, mouth rinse, toothpaste, and the like. One such device used to maintain proper oral health is the inter-dental brush device. An inter-dental brush device includes a handle and a brush attached to the end of the handle. The size and shape of the brush is designed to allow a user to insert the brush in-between the teeth to cleanse and massage, and remove tartar and food from the space along the gum line and in-between the teeth. Proper oral hygiene includes daily flossing or use of an inter-dental brush device. Many people prefer to use an inter-dental brush instead of floss because of its ease of use especially when the gap between the teeth is large. Over time, the brush portion of the inter-dental brush device wears out and the brush material becomes ineffective or defective in its teeth cleaning ability. At this point the entire inter-dental brush device, including the handle, must be discarded and replaced with a brand new inter-dental brush device.

Prior art inter-dental brush devices have a one size only brush head. Users must frequently discard the entire inter-dental brush device and replace it with a brand new one. Oftentimes, the user does not have a replacement inter-dental brush device on hand. Further, the process of continuously replacing the inter-dental brush device becomes rather costly. Accordingly, there remains a need in the art for an improved inter-dental brush device having an internal, replaceable brush cartridge that provides a continuous feed inter-dental brush portion.

The subject invention uses a continuous feedstock composed of inter-dental brush, which is coiled within a cartridge contained by the handle of the device. The continuous feedstock is generally wrapped around a pair of rotating swivels with one end of the continuous feedstock removably attached to one of the rotatable swivels. Due to the large wrap angle, which is in the range of 150 to 200 degrees, and preferably approximately 180 degrees, around each of the swivels, adequate friction is generated, thereby retaining the continuous feedstock against the swivels. The continuous inter-dental brush feedstock may have several layers of wraps each with a large wrap angle, thereby providing a long length of the inter-dental brush feedstock. The swivels have a brake mechanism preventing free running of the swivels as the feedstock is delivered. A knob provided on the handle is attached to a gear that feeds out the continuous feedstock of the inter-dental brush. The gear may push against the brush, but owing to the resiliency of the brush elements, damage to the brush element is prevented as it is fed out at the tip of the device. While the preferred embodiment of the invention uses a pair of swivels around which continuous feedstock of inter-dental brush is wrapped, a second embodiment uses a single roll within the cartridge. The feedstock is removably attached to the single roll and is tightly wound. The single roll has a brake to prevent free running of the single roll as the feedstock is fed out by the gear.

A brush cutter is provided in the angular portion of the handle, which slides out to cut the used, worn out inter-dental brush prior to operating the gear to advance a fresh inter-dental brush. The cutter cuts the wire portion of the inter-dental brush which carries the brush elements. The cutter is disposed on the underside face of the slidable cutter, which slides on two parallel grooves on the angular portion of the handle. When the cutting operation is complete, the cutter slides back into the angled portion of the handle.

FIG. 1 depicts generally at 10 a side view of the inter-dental brush device. The inter-dental device comprises a handle 11 comprising an elongated portion 12 and an angled portion 13 with a slidable cutter 13A. A continuous feed of inter-dental brush material 14 is housed in a cartridge 15 within the handle 11. The end of the continuous brush material is revealed, coming out through the center 16 of the angled portion of the handle. A gear 17 is controlled by a knob 18 mounted on the surface of the handle. The gear 17 operates to feed out more brush material as needed by the user. Two rotating swivels 19A, 19B contained within the cartridge 15 guide the brush material as it is fed out of the angled portion of the handle.

Figure 2:
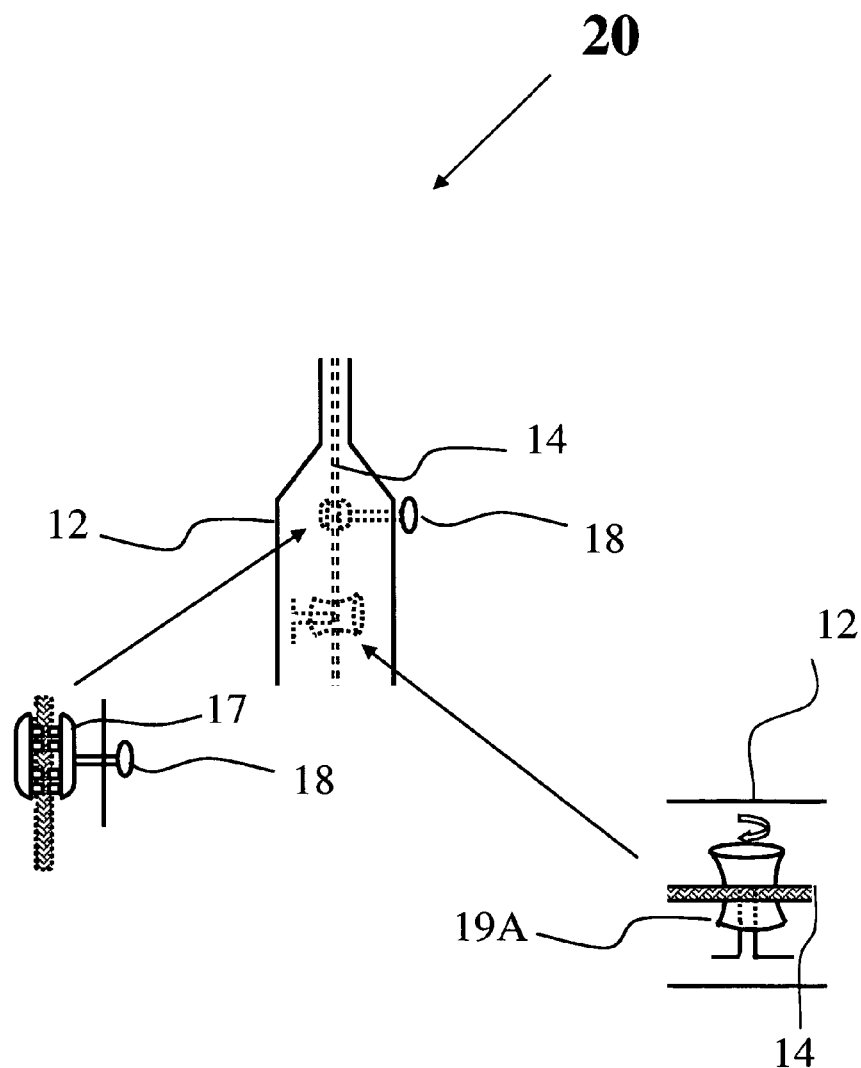
FIG. 2 depicts close up front view of the inter-dental brush showing the gear drive for delivering the fresh inter-dental brush and swivels within the cartridge that contains the continuous feedstock of inter-dental brush material.

FIG. 2 depicts generally at 20 a close up front view of the gear 17 attached to the knob 18 on the handle 12 and top swivel part 19A of the inter-dental device of the present invention. The gear 17 comprises a plurality of teeth adapted to grab onto the brush material as it passes out of the angled portion of the handle. The swivel 19A rotates as brush material is fed out. The continuous feed of brush material is spooled around the pair of swivels 19A and 19B as shown in FIG. 1.

Figure 3:
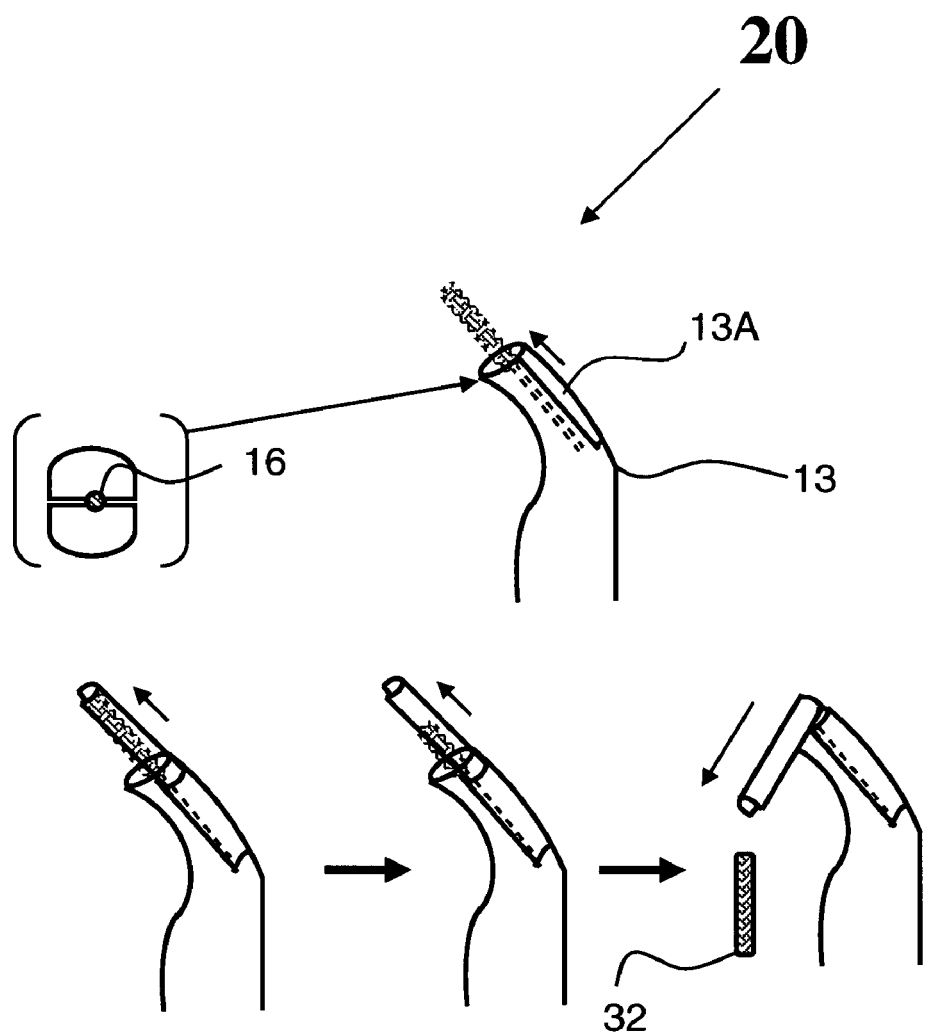
FIG. 3 depicts a slidable cutter on the angled portion of the handle, and adapted to cut off the used, worn out inter-dental brush prior to feeding out fresh inter-dental brush from the feedstock contained within the cartridge.

FIG. 3 depicts generally at 30 a close up side view of the angled portion 13 of handle 12, showing the operation of the slidable cutter 13A of the present invention. The angled portion of the handle comprises a moving slide cutter portion 13A, which is operable to cut off the unwanted portion of used brush material exiting the angled portion at 16 prior to feeding out new brush material from the device. The moving slide portion further comprises a cutter blade on its underside, which cuts off the used, worn out inter-dental brush 32, as shown. The moving slide portion moves along a channel section of the angled portion of the handle. The slidable cutter is moved back into the angled portion 13 of the handle after cutting the worn out inter-dental brush.

By providing an inter-dental brush device with a continuous feed of inter-dental brush material, the inter-dental device of the present invention enjoys a long service life with the ability to replace used and worn out inter-dental brush material with a fresh supply. Further, the inter-dental device includes an internal cartridge for storing an ample length of the inter-dental brush material. The diameter of the inter-dental brush can vary depending on the size of the tooth gaps to be serviced. Generally, the inter-dental brush has a diameter of about 0.25 to 0.125 inch. The inter-dental brush can have a conical configuration. In a preferred embodiment, the inter-dental brush comprises a series of conical shaped brushes in tandem. The inter-dental device makes the care of one's mouth, teeth, and gums much easier. The user is able to select the appropriate length of brush material to suit his particular tooth architecture. At the same time, the inter-dental device is very economical, because it uses replaceable inter-dental brush material cartridges. The inter-dental device is suitable for both travel and home use.

The key components of the continuous feed inter-dental brush and device include, in combination, the features set forth below:

1. a handle portion having an elongated portion and an angled portion;
2. a replaceable cartridge carrying a continuous feedstock of brush material;
3. a pair of swivels or a single roll contained within the cartridge, providing friction at the continuous feedstock-swivel interface;
4. a moving slide portion slidably mounted within the angled portion of the handle, the moving slide portion having a cutter blade on the underside to cut off used, worn out inter-dental brush; and
5. a knob controlling a gear with teeth that delivers fresh inter-dental brush from the continuous feedstock of inter-dental brush, whereby the continuous feedstock of brush material is spooled around the pair of swivels or a single roll, fed through the gear and fed out of the center of the angled portion of the handle, enabling a user to advance fresh brush material by turning the knob on the handle after sliding the moving slide portion to cut off the used worn out brush.

Having thus described the invention in rather full detail, it will be understood that such detail need not be strictly adhered to, but that additional changes and modifications may suggest themselves to one skilled in the art, all falling within the scope of the invention as defined by the subjoined claims.

What is claimed is:

1. An inter-dental brush, comprising:
   a. a handle that accepts replaceable cartridges of continuous inter-dental brush feedstock;
   b. said handle having an elongated portion and an angled portion;
   c. said angled portion having an aperture for feeding out said inter-dental brush;
   d. said angled portion having cutting means to cut off used, worn out inter-dental brush prior to feeding out fresh inter-dental brush, said cutting means including a slidable cutter having a pair of grooves in said angled portion of said handle; and
   e. said handle having delivery means to feed out said continuous inter-dental feedstock, whereby said used, worn out inter-dental brush is cut off by the user by said cutting means prior to feeding out fresh inter-dental brush by said delivery means.

2. An inter-dental brush as recited by claim 1, wherein said cartridge contains a pair of swivels around which said continuous inter-dental brush feedstock is wrapped.

3. An inter-dental brush as recited by claim 2, wherein one end of said continuous inter-dental brush feedstock is removably attached to one of said swivels.

4. An inter-dental brush as recited by claim 2, wherein said continuous inter-dental brush feedstock wraps around a swivel by a wrap angle ranging from about 150 to 200 degrees.

5. An inter-dental brush as recited by claim 2, wherein said swivels are provided with a braking means to prevent free running during feeding out of said feedstock.

6. An inter-dental brush as recited by claim 1, wherein said cartridge contains a single roll around which said continuous inter-dental brush feedstock is wrapped.

7. An inter-dental brush as recited by claim 6, wherein said single roll is provided with a braking means to prevent free running during feeding out of said feedstock.

8. An inter-dental brush as recited by claim 1, wherein said delivery means includes a gear feeding out said continuous inter-dental feedstock.

9. An inter-dental brush, comprising:
   a. a handle that accepts replaceable cartridges of continuous inter-dental brush feedstock;
   b. said handle having an elongated portion and an angled portion;
   c. said angled portion having an aperture for feeding out said inter-dental brush;
   d. said angled portion having cutting means to cut off used, worn out inter-dental brush prior to feeding out fresh inter-dental brush, said cutting means including a slidable cutter having a pair of grooves in said angled portion of said handle, and said slidable cutter having a cutting blade on an underside thereof; and
   e. said handle having delivery means to feed out said continuous inter-dental feedstock, whereby said used, worn out inter-dental brush is cut off by the user by said cutting means prior to feeding out fresh inter-dental brush by said delivery means.

10. An inter-dental brush as recited by claim 1, wherein said cartridge contains a pair of swivels around which said continuous inter-dental brush feedstock is wrapped.

11. An inter-dental brush as recited by claim 2, wherein one end of said continuous inter-dental brush feedstock is removably attached to one of said swivels.

12. An inter-dental brush as recited by claim 2, wherein said continuous inter-dental brush feedstock wraps around a swivel by a wrap angle ranging from about 150 to 200 degrees.

13. An inter-dental brush as recited by claim 2, wherein said swivels are provided with a braking means to prevent free running during feeding out of said feedstock.

14. An inter-dental brush as recited by claim 1, wherein said cartridge contains a single roll around which said continuous inter-dental brush feedstock is wrapped.

15. An inter-dental brush as recited by claim 6, wherein said single roll is provided with a braking means to prevent free running during feeding out of said feedstock.

* * * * *